(12) United States Patent
Wong

(10) Patent No.: US 8,195,274 B2
(45) Date of Patent: Jun. 5, 2012

(54) MAPPING OF VASCULAR PERFUSION TERRITORIES

(75) Inventor: Eric C. Wong, Del Mar, CA (US)

(73) Assignee: The Regents of the University of California, Oakland, CA (US)

(*) Notice: Subject to any disclaimer, the term of this patent is extended or adjusted under 35 U.S.C. 154(b) by 1043 days.

(21) Appl. No.: 12/111,133

(22) Filed: Apr. 28, 2008

(65) Prior Publication Data

US 2008/0269595 A1 Oct. 30, 2008

Related U.S. Application Data

(60) Provisional application No. 60/914,719, filed on Apr. 27, 2007.

(51) Int. Cl.
*A61B 5/05* (2006.01)
*G01V 3/00* (2006.01)

(52) U.S. Cl. ........ 600/419; 600/410; 324/309; 324/307; 324/306

(58) Field of Classification Search .................. 600/419, 600/410; 324/309, 307, 306
See application file for complete search history.

(56) References Cited

U.S. PATENT DOCUMENTS

| 6,271,665 | B1 | 8/2001 | Berr et al. | |
|---|---|---|---|---|
| 6,564,080 | B1 | 5/2003 | Kimura | |
| 7,587,233 | B2 * | 9/2009 | Wong et al. | 600/419 |
| 2005/0277825 | A1 | 12/2005 | Wong et al. | |
| 2005/0277828 | A1 * | 12/2005 | Alsop | 600/419 |

FOREIGN PATENT DOCUMENTS

WO WO 03/094725 11/2003

OTHER PUBLICATIONS

Trampel, Robert et al. Efficiency of Flow-Driven Adiabatic Spin Inversion Under Realistic Experimental Conditions: A Computer Simulation. Magnetic Resonance in Medicine 51:1187-1193 (2004).*

Alsop, D.C. and J.A. Detre, "Reduced transit-time sensitivity in noninvasive magnetic resonance imaging of human cerebral blood flow," J Cereb Blood Flow and Metab 16:1236-1249 (1996).

Davies, N. P. and P. Jezzard, "Selective arterial spin labeling (SASL): perfusion territory mapping of selected feeding arteries tagged using two-dimensional radiofrequency pulses," Magn Reson Med 2003;49(6):1133-1142 (2003).

Detre, J.A. et al., "Noninvasive Perfusion MR Imaging Using Spin Labeling Arterial Water," Chapter 15, Part V in *Diffusion and Perfusion: Magnetic Resonance Imaging: Applications to Functional MRI* (D. Le Bihan, Ed.), p. 296-305, Raven Press, New York, 1995.

(Continued)

*Primary Examiner* — Long V. Le
*Assistant Examiner* — Helene Bor
(74) *Attorney, Agent, or Firm* — Perkins Coie LLP

(57) ABSTRACT

Techniques, systems and computer program products are disclosed for mapping of vascular perfusion territories by placing one or more blood vessels of the vascular perfusion territories in a tag condition and others in a control condition by applying a train of pseudo-continuous radio frequency tagging pulses. In addition, an encoding scheme is applied to fully invert or relax the blood vessels of the vascular perfusion territories. Also, a tagging efficiency is measured for each blood vessel based on the applied encoding scheme. Further, the vascular perfusion territories are separated by using the measured tagging efficiency in a decoding process.

25 Claims, 12 Drawing Sheets

OTHER PUBLICATIONS

Edelman, R.R. et al., "Qualitative mapping of cerebral blood flow and functional localization with echo-planar MR imaging and signal targeting with alternating radio frequency," Radiology 192: 513-520 (1994).

Garcia, D.M. et al., "Pseudo-continuous flow driven adiabatic inversion for arterial spin labeling,". Proceedings of the International Society for Magnetic Resonance in Medicine, 13: 37 (2005).

Garwood and DelaBarre, "Advances in Magnetic Resonance—the return of the frequent sweep: designing adiabatic pulses for contemporary NMR," Journal of Magnetic Resonance 153: 155-177 (2001).

Garwood et al., "Symmetric Pulses to Induce Arbitrary Flip Angles with Compensation for RF Inhomogeneity and Resonance Offsets," Journal of Magnetic Resonance 94: 511-525 (1991).

Gunther, M., "Efficient visualization of vascular territories in the human brain by cycled arterial spin labeling MRI," Magn Reson Med 56(3):671-675 (2006).

Hendrikse, J., "Flow territory mapping of the cerebral arteries with regional perfusion MRI," Stroke 35:882-887 (2004).

Hennig et al., "Hyperechoes," Magnetic Resonance in Medicine 46: 6-12 (2001).

Kim, S.G. and N. V. Tsekos, "Perfusion imaging by a flow-sensitive alternating inversion recovery (FAIR) techniques: application to functional brain imaging," Magn. Reson. Med. 37: 425-435 (1997).

Kwong, K.K. et al., "Perfusion MR imaging," Proc. of the Society of Magnetic Resonance, vol. 2, Second meeting, Aug. 6-12, 1994, San Francisco, California, p. 1005.

Luh, et al., "QUIPSS II with thin-slice T1 Periodic Saturation: A Method for Improving Accuracy of Quantitative Perfusion Imaging Using Pulsed Arterial Spin Labeling," Magnetic Resonance in Medicine 41:1246-1254 (1999).

Norris, D. G., and C. Schwarzbauer, "Velocity Selective Radiofrequency Pulse Trains," Journal of Magnetic Resonance 137:231-236 (1999).

Paley, R.E.A.C., "On Orthogonal Matrices," Journal of Mathmatics and Physics 12:311-321 (1932-1933).

Parry, A. & P.M. Matthews, "Functional magnetic resonance imaging (fMRI): A 'window' into the brain," Oxford University, Centre for Functional Magnetic Resonance Imaging of the Brain (2002), 42 pages, Web site: http://www.fmrib.ox.ac.uk/fmri_intro/fmri_intro.htm [originally accessed on Aug. 20, 2003].

Wang, J. et al., "Amplitude-modulated continuous arterial spin-labeling 3.0-T perfusion MR imaging with a single coil: feasibility study," Radiology 235(1):218-228 (Apr. 2005).

Werner, R. et al., "Continuous artery-selective spin labeling (CASSL)," Magn Reson Med 53(5):1006-1012 (2005).

Wong, E.C., "Vessel Encoded Arterial Spin Labeling Using Pseudo-Continuous Tagging," Proceedings of the International Sociaty for Magnetic Resonance in Medicine 14:668 (2006).

Wong, E.C., "Vessel-encoded arterial spin-labeling using pseudocontinuous tagging," Magnetic Resonance in Medicine 58(6): 1086-1091 (2007).

Wong, E.C. and M. Cronin, "Velocity Selective Arterial Spin Labeling using an Adiabatic Hyperecho Pulse Train." Proc. Intl. Soc. Mag. Reson. Med. 11: 2181 (2003).

Wong et al., "Velocity Selective Arterial Spin Labeling," Proc. Intl. Soc. Mag. Reson. Med. 10: 621 (2002).

Wong et al., "Implementation of quantitative perfusion imaging techniques for functional brain mapping using pulsed arterial spin labeling," NMR in Biomedicine 10: 237-249 (1997).

Wong et al., "Quantitative imaging of perfusion using a single subtraction (QUIPSS and QUIPSS II)," Magn. Reson. Med. 39(5): 702-708 (1998).

Zaharchuk, G. et al., "Multiple perfusion and perfusion territory imaging in humans with separate label and image coils," Magn Reson Med 41(6):1093-1098 (1999).

Zimine, I. et al., "Dual vessel arterial spin labeling scheme for regional perfusion imaging," Magn Reson Med 56(5):1140-1144 (2006).

* cited by examiner

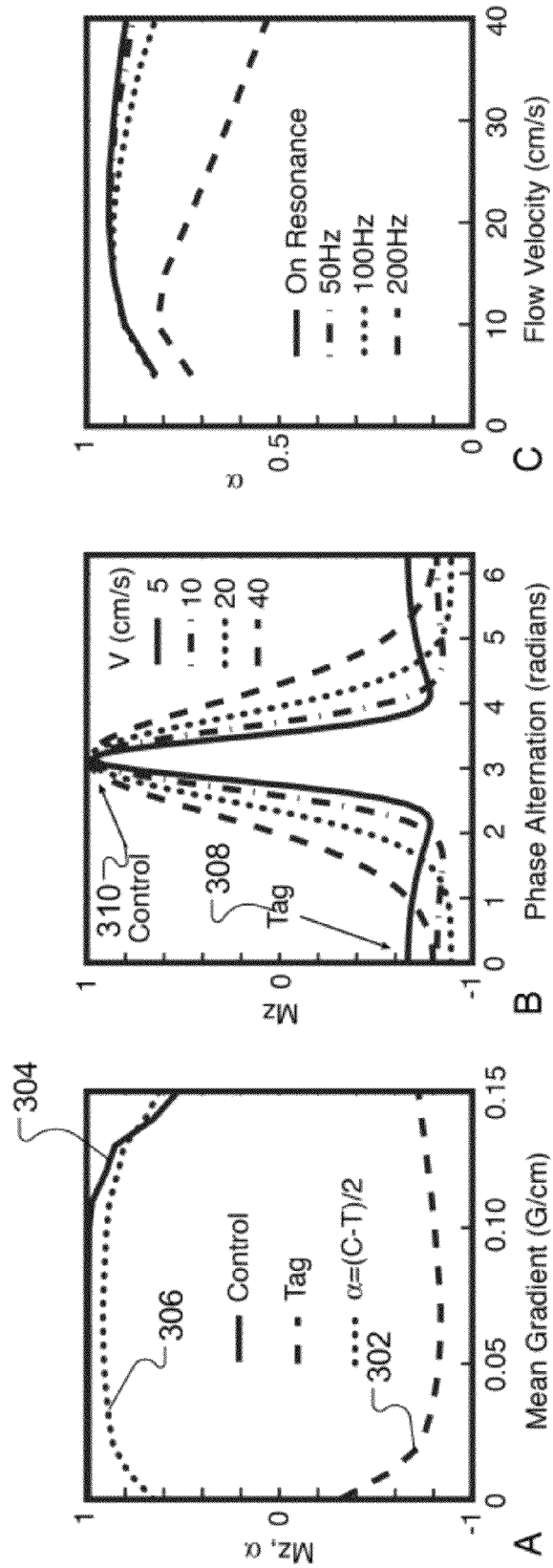

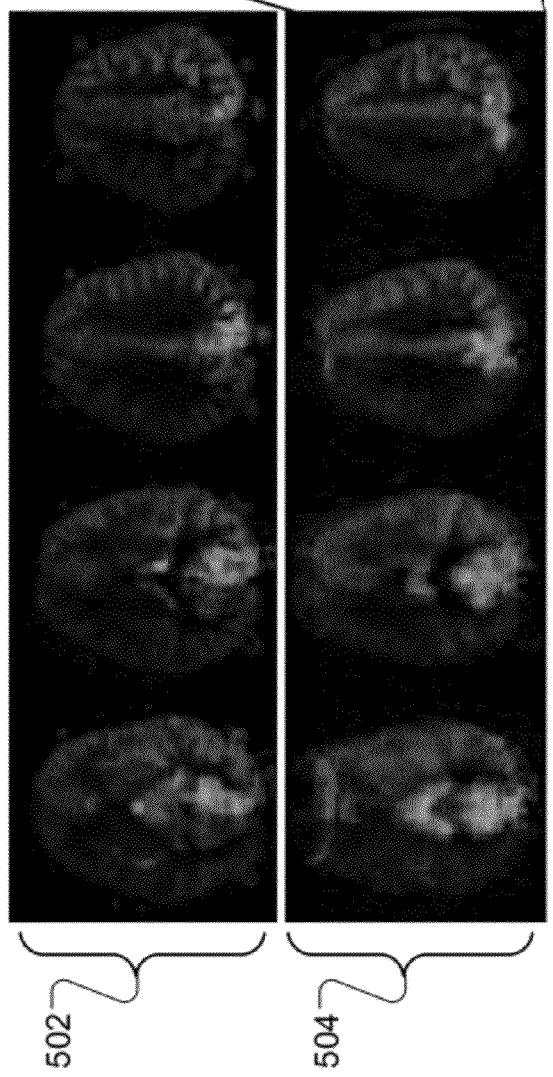
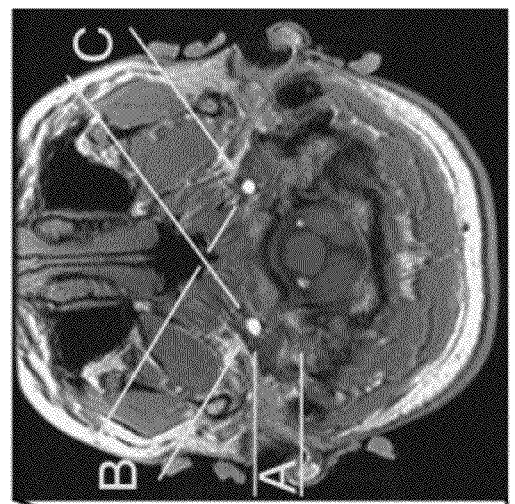
FIG. 5A
FIG. 5B

# MAPPING OF VASCULAR PERFUSION TERRITORIES

CLAIM OF PRIORITY

This application claims priority under 35 USC §119(e) to U.S. Patent Application Ser. No. 60/914,719, filed on Apr. 27, 2007, the entire contents of which are hereby incorporated by reference.

FEDERALLY SPONSORED RESEARCH OR DEVELOPMENT

This invention was made with government support under contract no. EB002096 awarded by National Institutes of Health (NIH). The government has certain rights in the invention.

BACKGROUND

This application relates to magnetic resonance imaging (MRI). Imaging through MRI techniques is well known and has been widely applied in imaging applications in medical, biological and other fields. In essence, a typical MRI technique produces an image of a selected body part of an object under examination by manipulating the magnetic spins in a body part and processing measured responses from the magnetic spins. A MRI system may include hardware to generate different magnetic fields for imaging, including a static magnetic field along a z-direction to polarize the magnetic spins, gradient fields along mutually orthogonal x, y, or z directions to spatially select a body part for imaging, and an RF magnetic field to manipulate the spins.

MRI techniques may be used to capture the functional changes in body parts or tissues such as the brain perfusion. One commonly-used technique for functional MRI is in vivo imaging by arterial spin labeling (ASL), where the arterial blood is tagged by magnetic inversion using RF pulses applied to a plane or slab of arterial blood proximal to the tissue of interest. Images are typically acquired with and without prior tagging of arterial blood and are subtracted to produce images that are proportional to perfusion. This magnetic tagging allows for the imaging of blood flow without the administration of dyes or other imaging agents. Hence, ASL provides non-invasive tagging in MRI measurements.

SUMMARY

Techniques, systems and apparatus are disclosed for non-invasive mapping of perfusion territories using MRI.

In one aspect, vascular perfusion territories are mapped by placing one or more blood vessels of the vascular perfusion territories in a tag condition and others in a control condition by applying a train of pseudo-continuous radio frequency tagging pulses. In addition, an encoding scheme is applied to fully invert or relax the blood vessels of the vascular perfusion territories. Also, a tagging efficiency is measured for each blood vessel based on the applied encoding scheme. Further, the vascular perfusion territories are separated by using the measured tagging efficiency in a decoding process.

Implementations can optionally include one or more of the following features. Applying the train of pseudo-continuous radio frequency tagging pulses can include selecting and tagging two or more of the blood vessels using arterial spin labeling in a tagging plane through which the vessels pass. Selecting and tagging the two or more of the blood vessels can include using pseudo-continuous arterial spin labeling. Also, pulses of magnetic field gradients can be applied across the tagging plane between the train of pseudo-continuous radio frequency pulses. In addition, two or more of the blood vessels can be differentially encoded within the tagging plane by using a modified pseudo-continuous arterial spin labeling. A single labeling gradient waveform can be applied in a direction of blood flow with non-zero mean for the tag and control conditions. Additional pulses of magnetic field gradients can be applied perpendicular to the single labeling gradient waveform to generate phase shifts between the blood vessels. Also, applying the encoding scheme can include using a Hadamard encoding scheme. Measuring the tagging efficiency can include measuring the tagging efficiency on a per-vessel basis to improve the decoding process. In addition, a perfusion can be quantitatively measured for each vascular perfusion territory. Further, a contribution of two or more of the blood vessels can be measured and quantified to the perfusion of each voxel. Applying the encoding scheme can include optimizing a signal-to-noise ratio. Also, the measured tagging efficiencies can be mapped to blood vessel coordinates. Measuring the tagging efficiencies can include measuring the tagging efficiencies by clustering.

In another aspect, the techniques described in this specification can be implemented using a magnetic resonance imaging (MRI) system that includes an MRI imaging module to acquire MRI image and a controller which controls the MRI imaging module. The controller is configured to control the MRI imaging module to perform operations including placing one or more blood vessels of the vascular perfusion territories in a tag condition and others in a control condition by applying a train of pseudo-continuous radio frequency tagging pulses; applying an encoding scheme to fully invert or relax the blood vessels of the vascular perfusion territories; measuring a tagging efficiency for each blood vessel based on the applied encoding scheme; and separate the vascular perfusion territories by using the measured tagging efficiency in a decoding process.

Implementations can optionally include one or more of the following features. The controller can be configured to apply the train of pseudo-continuous radio frequency tagging pulses comprises selecting and tagging two or more of the blood vessels using arterial spin labeling in a tagging plane through which the vessels pass. Also, the controller can be configured to select and tag the two or more of the blood vessels by using pseudo-continuous arterial spin labeling. The controller can be configured to apply pulses of magnetic field gradients across the tagging plane between the train of pseudo-continuous radio frequency pulses. Also, the controller can be configured to differentially encode two or more of the blood vessels within the tagging plane by using a modified pseudo-continuous arterial spin labeling. The controller can be configured to apply a single labeling gradient waveform in a direction of blood flow with non-zero mean for the tag and control conditions. The controller can be configured to apply additional pulses of magnetic field gradients perpendicular to the single labeling gradient waveform to generate phase shifts between the blood vessels. The controller can be configured to apply the encoding scheme comprising applying a Hadamard encoding scheme. The controller can be configured to measure the tagging efficiency comprising measuring the tagging efficiency on a per-vessel basis to improve the decoding process. The controller can be configured to quantitatively measure a perfusion of each vascular perfusion territory. The controller can be configured to measure and quantify a contribution of two or more of the blood vessels to a perfusion of each voxel. Further, the controller can be configured to apply the encoding scheme comprising optimizing a signal-to-noise ratio.

In another aspect, the techniques described in this specification can be implemented as a computer program product, embodied on a computer-readable medium, operable to cause a data processing apparatus to perform operations. For example, the computer program product can be operable to cause a data processing apparatus to place one or more blood vessels of the vascular perfusion territories in a tag condition and others in a control condition by applying a train of pseudo-continuous radio frequency tagging pulses. The computer program product can be operable to cause the data processing apparatus to apply an encoding scheme to fully invert or relax the blood vessels of the vascular perfusion territories. The computer program product can be operable to cause the data processing apparatus to measure a tagging efficiency for each blood vessel based on the applied encoding scheme. Further, the computer program product can be operable to cause the data processing apparatus to separate the vascular perfusion territories by using the measured tagging efficiency in a decoding process.

The subject matter described in this specification potentially can provide one or more of the following advantages associated with vessel encoded ASL imaging. For example, higher signal-to-noise ratio (SNR) can be achieved by using continuous rather than pulsed tagging. Better vessel selectivity can be obtained, as the vessel selection occurs within a single tagging plane through which the arteries are flowing. This is an improvement to the 3D slab or volume selective tag used in the pulsed methods that provide incomplete and spatially inhomogeneous separation of the feeding arteries. In addition, efficient and clear measurement can be obtained of the relative tagging efficiencies of each inflowing vessel, either for improved separation of the vessel encoded signal in post-processing, or for refined assignment of perfusion to a larger number of feeding arteries that there are encoding steps. Further, separation is possible of vascular territories above the Circle of Willis in the brain. While the volume and geometry of blood above the Circle of Willis renders pulsed methods extremely difficult, vessel encoded tagging within a single tagging plane can be efficient.

In addition, the subject matter described in this specification can also be implemented as a system including a processor and a memory coupled to the processor. The memory may encode one or more programs that cause the processor to perform one or more of the method acts described in this specification. Further the subject matter described in this specification can be implemented using various MRI machines.

BRIEF DESCRIPTION OF THE DRAWINGS

FIGS. 3A, 3B and 3C show examples of Bloch equation simulations of several features of a vessel encoding pulse train as shown in FIGS. 2B and 2C.

FIG. 4 C shows example encoding locations.

FIGS. 5A and 5B show examples of three vessel encoding from two additional subjects.

Like reference symbols and designations in the various drawings indicate like elements.

DETAILED DESCRIPTION

The techniques and systems described in this application can enable non-invasive mapping of perfusion territories using MRI. In particular, a person can be placed in an MRI scanner, and without the use of any exogenous agents, map the tissue regions of the person that are supplied with blood from different feeding arteries.

This particular implementation is within a class of MR imaging methods known as arterial spin labeling (ASL). There are pulsed ASL methods that tag the magnetization of arterial blood using short radiofrequency pulses, and continuous ASL methods that tag arterial blood using long trains of RF pulses and flow driven adiabatic inversion. Each of these classes of ASL methods includes sub-classes that allow for the tagging process to be selective for specific arteries. The two pulsed ASL and two continuous ASL methods are limited to imaging one perfusion territory at a time. In addition, there are two pulsed methods that may enable more time efficient encoding of perfusion data from two or more vessels simultaneously. Time efficiency of these methods can reduce the scan times from impractical (10-15 min) to practical (5 min) for various clinical applications. The present techniques and systems as described in this specification can improve vessel encoded ASL imaging.

In vascular territory imaging (VTI), blood in individual or groups of feeding arteries can be tagged using ASL, and images can be acquired that map the vascular distribution of those feeding arteries. Potential clinical applications for the mapping of vascular territories include the evaluation of vascular stenoses and the mapping of blood supplies to tumors. VTI can be performed sequentially for two or more vascular territories in order to develop a complete map of the blood supply to the target tissue.

Based on techniques described in this specification, multiple vascular territories can be mapped by tagging combinations of vessels in encoding schemes that enable efficient generation of vascular territory maps. The vessel encoded approach can be implemented based on pseudo-continuous tagging to provide high SNR tagging as well as good vessel selectivity and flexibility in tagging geometry.

Vessel Encoded Arterial Spin Labeling Using Pseudo-Continuous Tagging

Figure 1:
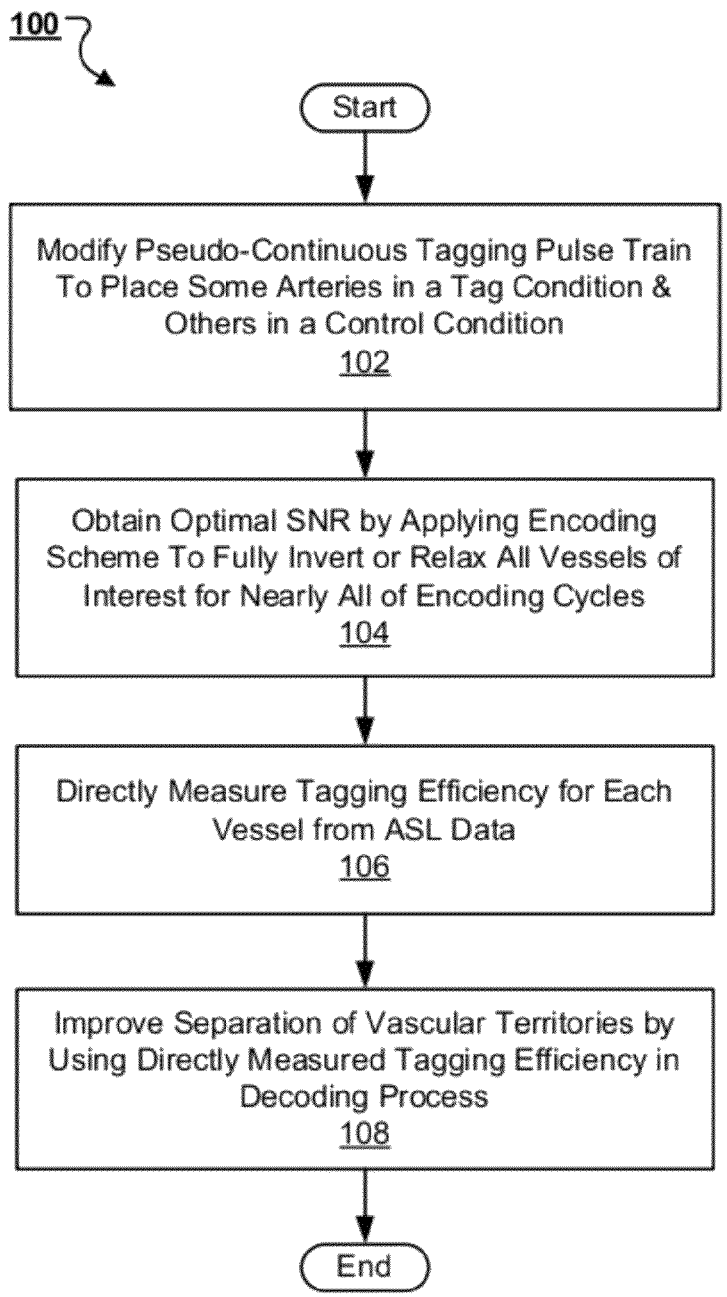
FIG. 1 shows an example process for SNR efficient mapping of vascular territories based on pseudo-continuous ASL.

FIG. 1 shows an example process 100 for SNR efficient mapping of vascular territories based on pseudo-continuous ASL. A pseudo-continuous tagging pulse train is modified 102 using additional transverse gradient pulses and phase cycling to place some arteries in a tag condition and others passing through the same tagging plane in a control condition. This is combined with a Hadamard or similar encoding scheme such that all vessels of interest are fully inverted or relaxed for nearly all of the encoding cycles, providing 104 optimal SNR. The relative tagging efficiency for each vessel is measured 106 directly from the ASL data and is used in the decoding process to improve 108 the separation of vascular territories. High SNR maps of left carotid, right carotid, and basilar territories can be generated in 6 minutes of scan time, for example.

Vessel Encoding

In non-vessel encoded ASL, the scan consists of two image types. Both image types contain identical static tissue signal but differ in the sign of the inflowing arterial magnetization. This encoding process can be described mathematically by y=Ax where x is the contribution to the signal from inflowing blood and static tissue components, A is the encoding matrix, and y is the resulting signal intensities as shown in Equation (1) below.

$$y = \begin{bmatrix} y_1 \\ y_2 \end{bmatrix} \quad [1]$$

$$A = \begin{bmatrix} -1 & 1 \\ 1 & 1 \end{bmatrix}$$

$$x = \begin{bmatrix} V \\ S \end{bmatrix}$$

In Equation (1) above, V is the MR signal of inflowing blood and S is the MR signal of static tissue. The rows of A are the encoding steps necessary to generate $y_1$ and $y_2$, which are typically referred to as 'tag' and 'control' images. The ASL signal V can be recovered by subtraction of $y_2-y_1$. More formally, when A has a pseudo-inverse $A^+$, x can be reconstructed by inversion to yield $x=A^+y$ as shown in Equation (2) below.

$$\begin{bmatrix} V \\ S \end{bmatrix} = A^+ y = 0.5 * \begin{bmatrix} -1 & 1 \\ 1 & 1 \end{bmatrix} \begin{bmatrix} y_1 \\ y_2 \end{bmatrix}, \quad [2]$$

Thus, the same result is obtained that V is proportional to $y_2-y_1$.

In order to separately encode the contribution of more than one vessel to the MR signal, more than two encoding steps may be necessary, in which the vessels of interest are encoded in different patterns. The three-vessel encoding scheme as described in Gunther (Gunther M. Efficient visualization of vascular territories in the human brain by cycled arterial spin labeling MRI. Magn Reson Med 2006; 56(3):671-675) is shown in Equation (3).

$$\begin{bmatrix} y_1 \\ y_2 \\ y_3 \\ y_4 \end{bmatrix} = \begin{bmatrix} -1 & 1 & -1 & 1 \\ 1 & -1 & -1 & 1 \\ -1 & -1 & 1 & 1 \\ 1 & 1 & 1 & 1 \end{bmatrix} \begin{bmatrix} R \\ L \\ B \\ S \end{bmatrix} \quad [3]$$

and thus $$\begin{bmatrix} R \\ L \\ B \\ S \end{bmatrix} = 0.25 * \begin{bmatrix} -1 & 1 & -1 & 1 \\ 1 & -1 & -1 & 1 \\ -1 & -1 & 1 & 1 \\ 1 & 1 & 1 & 1 \end{bmatrix} \begin{bmatrix} y_1 \\ y_2 \\ y_3 \\ y_4 \end{bmatrix},$$

where R, L, and B are the contributions of tagged blood signal from the right carotid, left carotid, and basilar arteries, respectively. In both of the above examples, the encoding matrix consists of columns from a Hadamard matrix (Paley REAC. On Orthogonal Matrices. Journal of Mathematics and Physics 1933; 12:311-320). The resultant encoding is SNR optimal in the sense that all inflowing blood is either fully inverted or fully relaxed for each tagging cycle, and there are equal numbers of tag and control conditions for each vessel. All encoding matrices that consist of columns from a Hadamard matrix will have these properties, even if they are not square, and decoding of this type of data amounts to simple subtraction of the tag from control images for each vessel. In general, vessel geometry and tagging methodology may not allow for optimal encoding, but the expected SNR efficiency can be calculated from the decoding matrix $A^+$. For unit signal and unit noise, the decoding process outlined above will produce unit signal, because it is a direct inversion of the encoding process, while the noise for each territory will be given by the square root of the sum of squared elements across a row of $A^+$. For comparison, the SNR for simple averaging across N samples with unit signal and noise per sample is $\sqrt{N}$. A ratio of these SNR values can be represented as an index E of SNR efficiency as shown in Equation (4).

$$E_i = \frac{SNR_{encoded}}{SNR_{averaging}} = \frac{1 / \sqrt{\sum_j A_{i,j}^{+2}}}{\sqrt{N}} = \frac{1}{\sqrt{N \sum_j A_{i,j}^{+2}}}, \quad [4]$$

where N is the number of samples (and therefore the number of columns in $A^+$). For any Hadamard encoding scheme, E=1.

Tagging Method

The modulation of tag and control states can be accomplished using either pulsed or continuous ASL methodology. In this specification, the focus is on one or more modifications of the pseudo-continuous ASL (PCASL) tagging technique (Garcia DM, de Bazelaire C, Alsop D. Pseudo-continuous flow driven adiabatic inversion for arterial spin labeling. Proceedings of the International Society for Magnetic Resonance in Medicine; 2005; Miami. p 37) that provides efficient modulation of tag and control states across vessels within a single tagging plane.

In PCASL, a train of closely spaced RF pulses, in conjunction with a synchronously pulsed gradient field, effects a flow driven adiabatic inversion as blood flows through the tagging plane. Requirements for both the mean gradient and the mean RF amplitude to satisfy adiabatic conditions are similar to those of continuous ASL, and the mechanism of tagging is identical. Because the RF is applied in the presence of a larger gradient than in continuous ASL, the RF irradiation is farther off resonance in the target tissue, and magnetization transfer effects are greatly reduced (Garcia DM, de Bazelaire C, Alsop D. Pseudo-continuous flow driven adiabatic inversion for arterial spin labeling. Proceedings of the International Society for Magnetic Resonance in Medicine; 2005; Miami. p 37.) In PCASL, additional transverse gradient pulses can be applied during the time gaps in between the RF pulses to modulate the relative phase of spins in different vessels within the tagging plane.

The PCASL technique is modified to enable differential encoding of vessels within the inversion plane. In one modification, a single labeling gradient waveform is applied in the direction of flow with non-zero mean for both tag and control conditions. In another modification, additional gradients are applied perpendicular to the labeling gradient to generate phase shifts between the vessels of interest. In yet another modification, RF phase modulation is applied across pulses to place the vessels of interest in tag and control conditions according to the encoding schedule. These modifications can be defined as vessel encoded pseudo-continuous ASL (VEP- CASL) techniques where two or more vessels flowing through the tagging plane are differentially tagged and encoded across image repetitions.

Figure 2A:
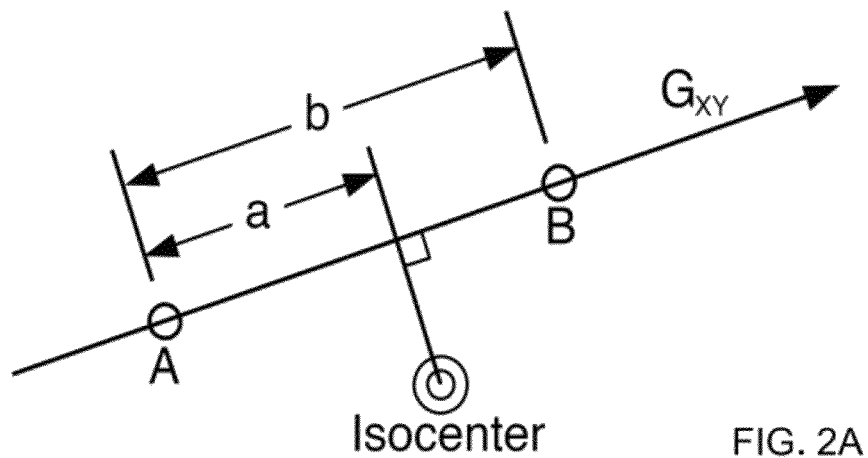
FIG. 2A shows an example of a diagram of tagging geometry for two vessels A and B, separated by distance b.
Figure 2B:
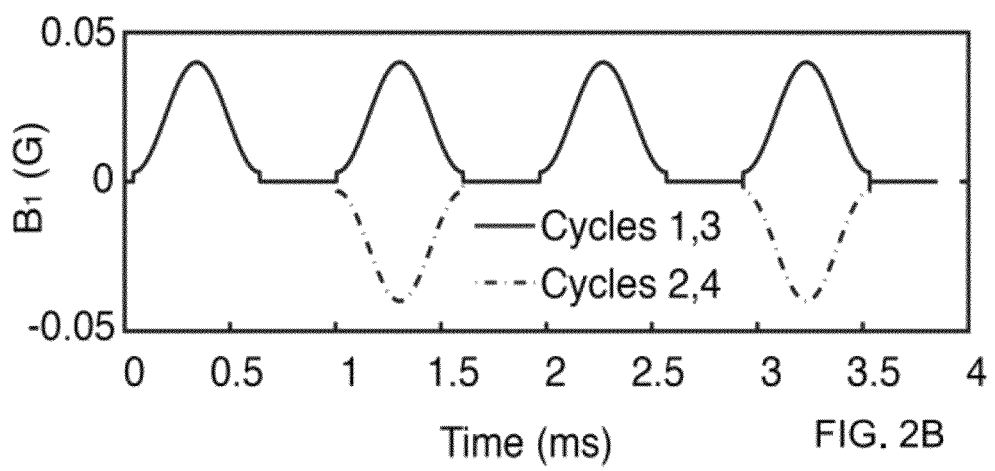
FIG. 2B shows an example of RF waveforms for a small segment of the tagging pulse train.
Figure 2C:
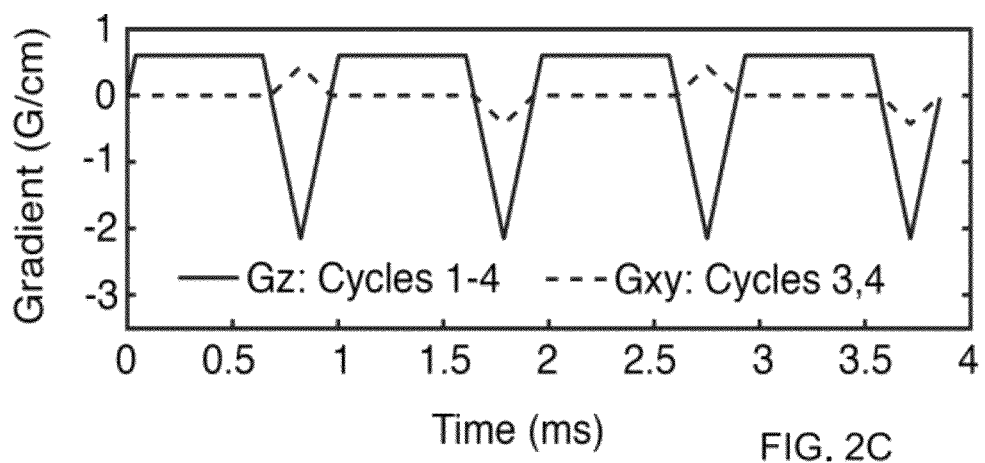
FIG. 2C shows an example of gradient waveforms for a small segment of the tagging pulse train for four cycles.

FIGS. 2A, 2B and 2C show examples of a tagging geometry and a pulse train for four cycles. FIG. 2A shows an example of a diagram of tagging geometry for two vessels A and B, separated by distance b. Within the tagging plane, $G_{xy}$ is applied along the line from one vessel to the other, and vessel A is a distance from the projection of the isocenter onto this line. FIG. 2B shows an example of RF waveforms for a small segment of the tagging pulse train. FIG. 2C shows an example of gradient waveforms for a small segment of the tagging pulse train. Cycle 1 represents having all vessels inverted. Cycle 2 represent having no vessels inverted. Cycle 3 represents having only vessel A inverted. Cycle 4 represents having only vessel B inverted. In non-modified pseudo-continuous ASL, the labeling gradient ($G_z$) has non-zero mean for the tag condition and zero mean for the control condition (Garcia DM, de Bazelaire C, Alsop D. Pseudo-continuous flow driven adiabatic inversion for arterial spin labeling. Proceedings of the International Society for Magnetic Resonance in Medicine; 2005; Miami. p 37.) While it is sensible to use a gradient with zero mean for the control condition, this is not necessary in order to obtain a transparent control pulse (see RF pulse simulations below). For all four cycles the same tagging gradient in the direction of flow is used. For cycles 3 and 4, an additional gradient pulse ($G_{xy}$) is applied between RF pulses in the direction of the vector from one vessel to the other within the tagging plane. This pulse is applied with alternating sign and an area of $\pi/\gamma b$, where b is the separation between vessels, producing a phase shift of $\pi$ between the two vessels. If the phases of the RF pulses are adjusted so that all pulses are coherent with spins at the location of one vessel, then spins in that vessel experience adiabatic inversion, while spins in the other vessel experience pulses with alternating sign, resulting in a transparent pulse. The phase modulation across the RF pulse train for the 4 cycles is summarized as:

Cycle 1:

$$\phi_i = \phi_z$$

Cycle 2:

$$\phi_i = \phi_z + (i \bmod 2)\pi$$

Cycle 3:

$$\phi_i = \phi_z + \phi_{xyA}$$

Cycle 4:

$$\phi_i = \phi_z + \phi_{xyB}$$

$$\phi_z = i\gamma \overline{G}_z t z \, \phi_{xyA} = (i \bmod 2)\pi(a/b) \, \phi_{xyB} = (i \bmod 2)\pi((b-a)/b) \quad [5]$$

where i is the pulse number, $\overline{G}_z$ is the mean value of $G_z$, t is the RF pulse spacing, z is the offset of the labeling plane from isocenter, 'mod' is the integer modulus function, and a and b are the vessel location and separation as shown in FIG. 2. The variable $\phi_z$ is the phase needed to keep the pulses coherent with spins under the influence of $G_z$, while $\phi_{xyA}$ and $\phi_{xyB}$ are the additional phases needed to keep the pulses in phase with spins in vessels 1 and 2, respectively, in the presence of $G_{xy}$. This encoding method generates alternating lines of tag and control conditions within the tagging plane.

Methods

Tagging Pulse Train Simulations

The effect of the mean gradient phase alternation, flow velocity, and resonance offset can be calculated by Bloch equation simulation for the following pulse train parameters: Hanning shaped RF pulses of 600 s duration and 0.04 G amplitude; gradient amplitude of 0.6 G/cm during RF pulses, with refocusing lobes applied at a slew rate of 15 G/cm/ms and a maximum magnitude of 4 G/cm. The flip angle at the center of the pulse profile is 20°, and the width over which the flip angle exceeds 2° is 2.0 cm. For the simulations, $T_2$ can be assumed to be 200 ms, and $T_1$ relaxation can be neglected in order to simplify the calculation of the tagging efficiency.

Imaging Parameters

Imaging is performed on a General Electric (Waukesha, Wis.) 3T scanner using a commercial 8-channel head RF coil array and the body coil for RF transmission, for example. The volunteers to be included in the scan group can include both male and female individuals of a predetermined age range. For example, four normal volunteers, two male and two female, of ages 25-45 were included in the scan group. The volunteers are scanned with prior informed consent under an IRB approved protocol. The FOV is determined to be 24 cm×8 mm with a 2 mm gap between slices, and single-shot 2D spiral readout is used. Tagging parameters include those described in the simulations above, with a total length of 1574 ms for the tagging pulse train, composed of 1640 RF pulses with a spacing of 960 s. Two non-selective adiabatic inversion pulses are applied 950 ms and 300 ms prior to image acquisition for background suppression. The post labeling delay is 1000 ms and TR was 3000 ms. Twenty images are acquired for each cycle of the encoding scheme, resulting in a scan time of 4 minutes for 2-vessel encoding, and 6 or 8 minutes for 3-vessel encoding. Mean and RMS B1 are 0.014 G and 0.020 G, respectively, during the tagging pulse train and the average whole body SAR reported by the integrated RF power monitor in the scanner was 1.7-1.8 W/Kg.

Data Processing

Vascular territory maps can be generated by pseudo-inversion of the encoding matrix as described above. Ideally, each vessel of interest is fully inverted or fully relaxed during each tagging period. In practice, because of vessel geometries and velocity distributions, this may not be always possible. In order to correct for this, the tagging efficiencies of the vessel encoded scans can be measured relative to non-selective scans and included in the encoding matrix. From the non-selective scan cycles of the encoding process (all vessels relaxed or all vessels inverted), a conventional ASL image can be calculated by simple subtraction. A signal intensity threshold is set, for example, at half of the intensity at the 99th percentile in this image, and voxels above this threshold is identified as a rough gray matter mask. Within this mask, the ratio of signal intensities for vessel encoded scans divided by non-selective scans is calculated on a voxel-wise basis and displayed as histograms. Local peaks in these histograms are fitted to Gaussian functions by least squares fitting to provide estimates of the tagging efficiency of each tagged vessel, relative to the tagging efficiency of the non-vessel encoded scan. These relative tagging efficiencies are referred to as $\beta$, and can be applied directly in the construction of the encoding matrices. No spatial smoothing or masking of signal outside the brain is applied, and images are displayed according to radiological convention (left of image is right of subject).

FIGS. 3A, 3B and 3C show examples of Bloch equation simulations of several features of a vessel encoding pulse train as shown in FIG. 2. FIG. 3A shows the calculated $M_z$ of spins of blood that have flowed through the tagging plane as a function of the mean tagging gradient $\overline{G}_z$, averaging across velocities from 5-40 cm/s. In the control condition 304 with RF alternation, the pulse train is transparent for $\overline{G}_z \leq 0.1$ G/cm. In other words, with a phase alternation of $\pi$ between RF pulses, the perturbation of flowing spins is minimal for $\overline{G}_z$ from 0-0.1 G/cm, producing an efficient control condition across this range of mean gradients. In the absence of phase modulation (the tag condition) 302, efficient flow driven inversion occurs from approximately 0.04-0.12 G/cm, and the tagging efficiency 306 $\alpha = (M_{z,control} - M_{z,tag})/2$ has a broad peak centered at approximately $\bar{G}_z = 0.08$ G/cm. This value of $\bar{G}_z$ is used throughout in this specification.

FIG. 3B shows an example of a calculated response of $M_z$ as a function of RF phase alternation for a range of flow velocities. At locations between the two vessels of interest, intermediate values of $M_z$ are obtained. A vessel in the tag condition 302 experiences zero phase alternation 308, while one in the control condition experiences an alternation of $\pi$ radians 310 from pulse to pulse. In the control condition, a phase shift of $\pi$ radians per pulse is applied to make the pulse train transparent. Vessels in other locations experience intermediate levels of phase alternation according to their position along $G_{xy}$. From these curves one can calculate the expected tagging efficiency as a function of vessel position and velocity.

FIG. 3C shows the sensitivity of this tagging scheme to resonance offset. The tagging efficiency vs. resonance offset is calculated. Above 100 Hz resonance offset, a marked reduction of tagging efficiency is shown.

Figures 4A, 4B, 4C:
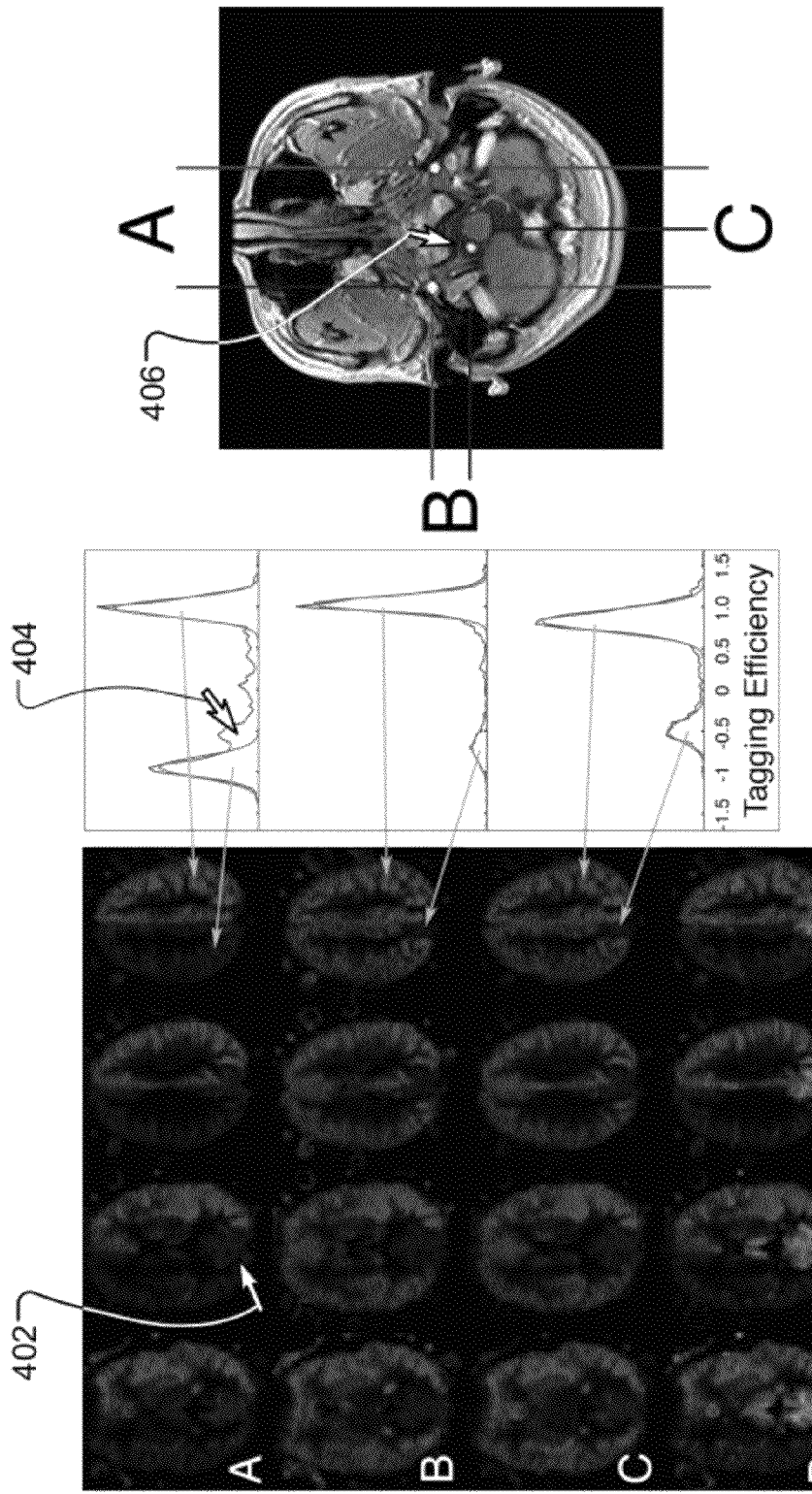
FIG. 4A show an example of vessel encoded images from one subject.
FIG. 4B shows example histograms of the measured tagging efficiencies for each encoding scheme.

FIGS. 4A, 4B and 4C show examples of vessel encoded images from one subject. In FIG. 4A, rows A, B, and C show the results of three different two-vessel encoding schemes, with the encoding locations shown in FIG. 4C. In row A, the left and right carotid arteries are encoded and separable with high efficiency, but the posterior circulation cannot be clearly separated from the anterior circulation. In this subject, the right vertebral artery is dominant, and the posterior territory appears in the histogram as a peak with $\beta \approx -0.5$ (see while arrows 402, 404, 406). In row B, the anterior and posterior circulations are separated using anterior/posterior encoding, while in row C, the same separation is accomplished using left/right encoding, but with lower measured $\beta$ for all vessels. Row D shows a three vessel separation based on the data from rows A and B.

FIG. 4B shows example histograms of the measured tagging efficiencies for each encoding scheme. With perfect tagging efficiency the encoding and decoding matrices and SNR efficiency for this separation can be calculated as shown in Equation (6).

$$A = \begin{bmatrix} -1 & -1 & -1 & 1 \\ 1 & 1 & 1 & 1 \\ -1 & 0 & 1 & 1 \\ 1 & 0 & -1 & 1 \\ 1 & -1 & 1 & 1 \\ -1 & 1 & -1 & 1 \end{bmatrix} \quad [6]$$

$$A^+ = \begin{bmatrix} -.125 & 0.125 & -0.25 & 0.25 & 0.125 & -0.125 \\ -0.25 & 0.25 & 0 & 0 & -0.25 & 0.25 \\ -0.125 & 0.125 & 0.25 & -0.25 & 0.125 & -0.125 \\ 0.167 & 0.167 & 0.167 & 0.167 & 0.167 & 0.167 \end{bmatrix}$$

$$E = \begin{bmatrix} 0.943 \\ 0.817 \\ 0.943 \\ 1 \end{bmatrix},$$

where the columns of A correspond to the right carotid, basilar, left carotid, and static tissue components, respectively, and the rows represent 6 encoding cycles. The theoretical SNR efficiency is not 1 because 2 of the 6 encoding cycles generate zero signals from the basilar artery. Using the values of $\beta$ measured from the histograms shown in FIG. 4B, Equation (6) can be rewritten as shown in Equation (7).

$$A = \begin{bmatrix} -1 & -1 & -1 & 1 \\ 1 & 1 & 1 & 1 \\ -0.99 & 0.50 & 1.04 & 1 \\ 0.99 & -0.50 & -1.04 & 1 \\ 1.01 & -0.71 & 1.01 & 1 \\ -1.01 & 0.71 & -1.01 & 1 \end{bmatrix} \quad [7]$$

$$A^+ =$$

$$\begin{bmatrix} -.179 & 0.179 & -0.247 & 0.247 & 0.078 & -0.078 \\ -0.293 & 0.293 & 0 & 0 & -0.291 & 0.291 \\ -0.029 & 0.029 & 0.247 & -0.247 & 0.214 & -0.214 \\ 0.167 & 0.167 & 0.167 & 0.167 & 0.167 & 0.167 \end{bmatrix}$$

$$E = \begin{bmatrix} 0.918 \\ 0.700 \\ 0.880 \\ 1 \end{bmatrix}.$$

Across four subjects, the average value of $\beta$ is 0.94±0.07 in the carotid arteries, and across three subjects 0.69±0.14 in the vertebral arteries.

FIGS. 5A and 5B show examples of three vessel encoding from two additional subjects. In the top row 502, the encoding method is identical to that used for FIG. 4A, row D, but in this subject, the basilar circulation supplied only the left posterior cerebral territory, which was consistent with MR angiographic findings. In addition, the right anterior cerebral territory appears to be supplied by mixed left and right carotid blood suggesting active flow in the anterior communicating artery. In the lower row 504, an 8 cycle Hadamard scheme is used to encode the vessels in the neck as shown in FIG. 5B. Each of the vessel encodings A, B, and C, as shown in FIG. 5B, contrast two vessels with the third. While the theoretical values of E for this encoding are [1, 1, 1, 1], the measured $\beta$ ranged from 0.54-0.91, and the SNR efficiency is E=[0.88, 0.80, 0.89, 1].

Figures 6A, 6B:
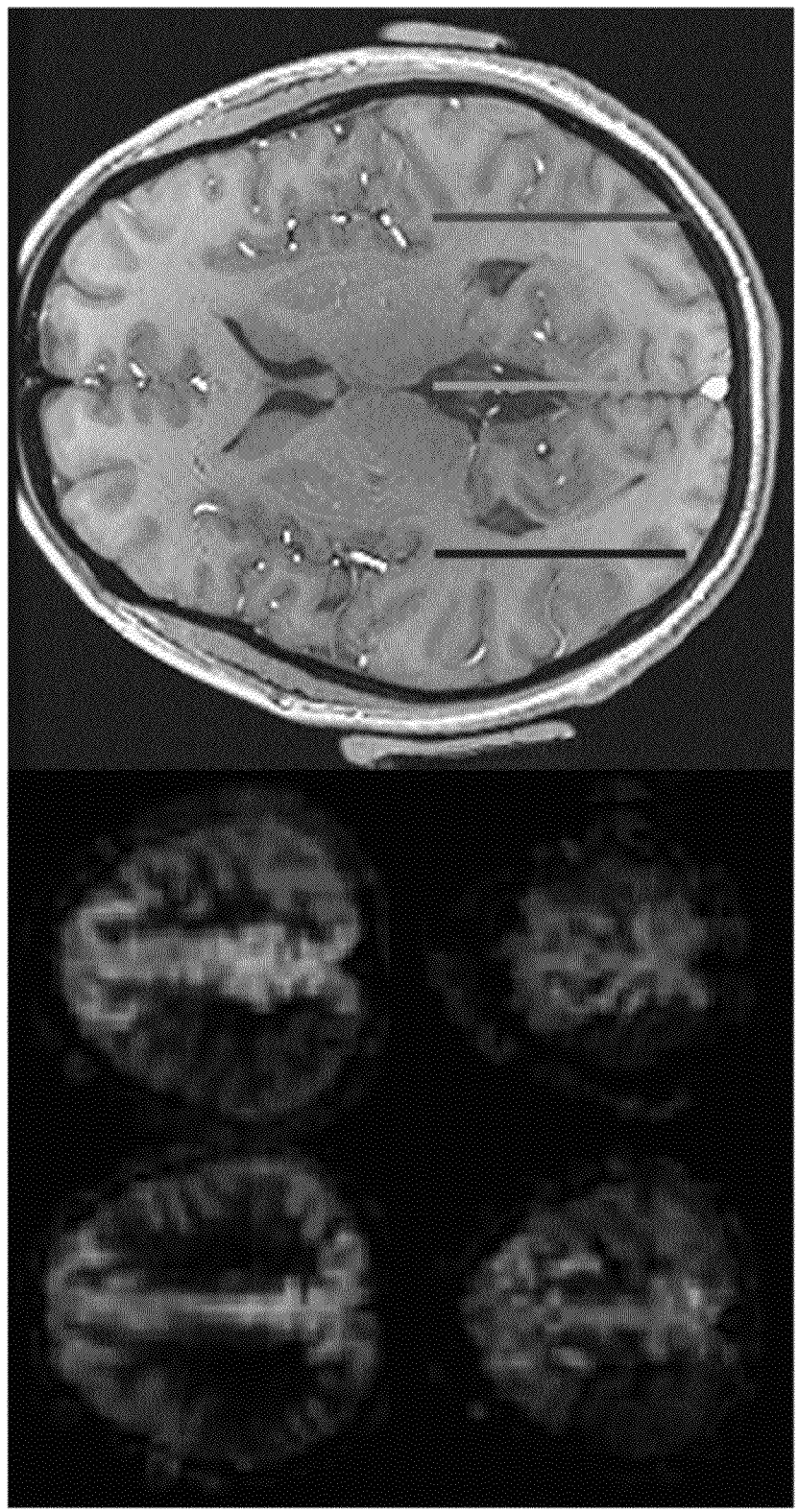
FIGS. 6A and 6B show an example of vessel encoding above the Circle of Willis.

FIGS. 6A and 6B show an example of vessel encoding above the Circle of Willis. In this example, three vascular territories, left middle cerebral artery (MCA), anterior cerebral artery (ACA), and right MCA, are mapped using left/right encoding, analogous to scans A and C in FIG. 4A. While the ACA and some branches of the MCA along the insula are tagged with high efficiency, there are other branches of the MCAs that are not well tagged, hence the incomplete representation of the anterior portion of the MCA territories. For left MCA, ACA, and right MCA, E=[0.85, 0.82, 0.85].

Figure 7:
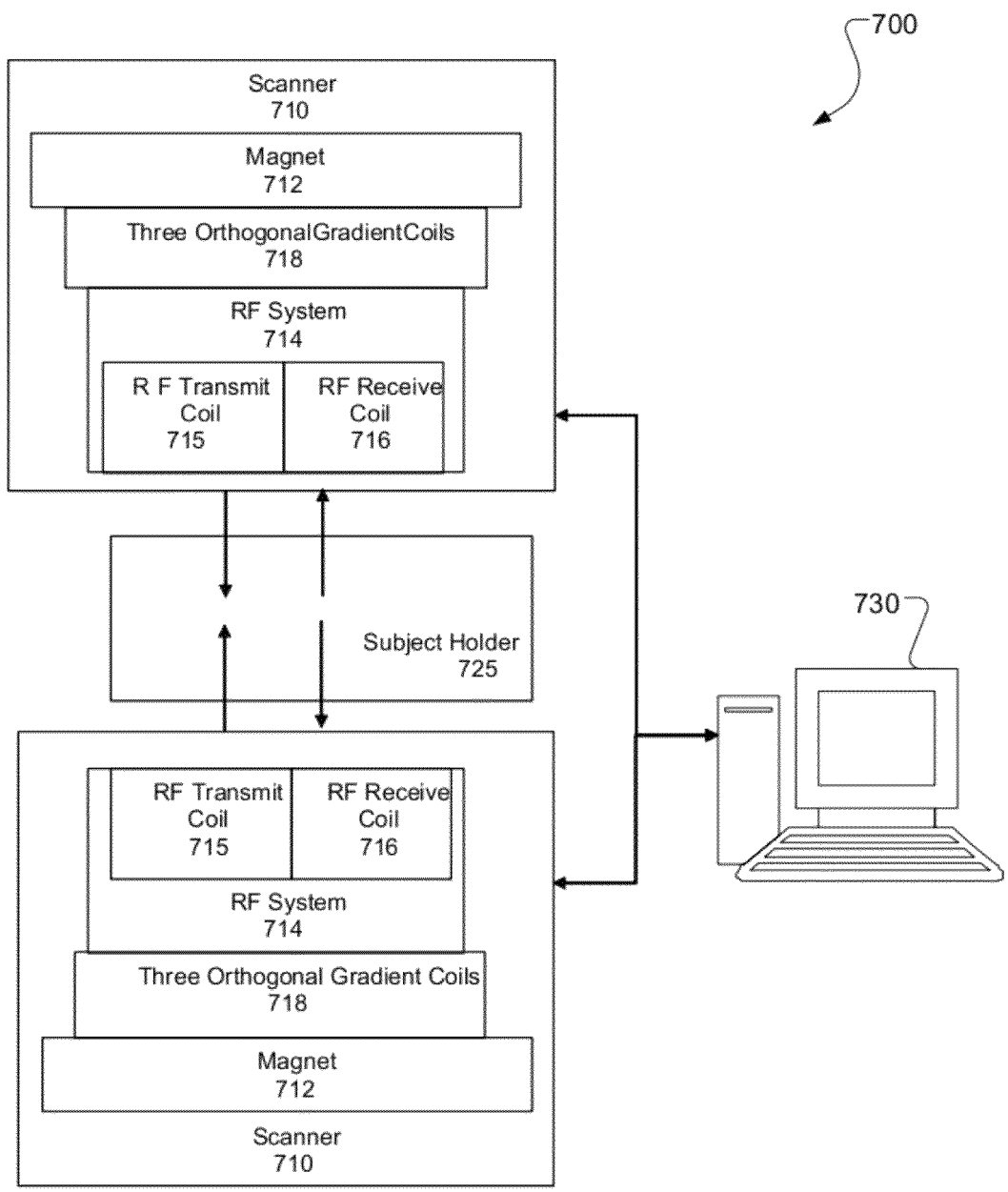
FIG. 7 shows an example of an MRI system.

FIG. 7 shows an example MRI system 700. Techniques as disclosed in this specification can be implemented using the MRI system 700. The MRI system 700 can be implemented using any one of various MRI scanners such as a 1.5 T Sigma TwinSpeed scanner (available from GE Healthcare Technologies, Milwaukee, Wis.) The MRI system 700 includes a scanner 710, a data processing apparatus 730 and a subject holder or table 725 for holding a subject 720. The scanner 710 includes a main magnet 712, three orthogonal gradient coils 718 and a RF system 714. The main magnet 712 is designed to provide a constant, homogeneous magnetic field. The three orthogonal gradient coils 718 are designed to provide three orthogonal, controller magnetic gradients used to acquire image data of a desired slice by generating an encoded and slice-selective magnetic field. The RF system 714 includes a RF transmit coil 715 and a RF receive coil designed to transmit and receive RF pulses. The RF system 745 can further include a RF synthesizer (not shown) and a power amplifier (not shown). In some implementations, an integrated transceiver coil (not shown) can be implemented instead of the separate transmit coil 715 and receive coil 716 for transmitting and receiving RF signals. For example, a close-fitting smaller coil can improve image quality when a small region is being imaged. Further, various types of coils that are placed around specific parts of a body (e.g., the head, knee, wrist, etc.) or even internally can be implemented depending on the sample and imaging applications.

The MRI system 700 is designed to perform the techniques disclosed in this specification. In particular, the MRI system 700 is designed to implement the methods disclosed with respect to FIG. 1. The RF system 714 is designed to apply to a target subject 720 a non-selective inversion RF pulse, a slice-selective inversion RF pulse and a half RF excitation pulse. The three orthogonal coils 718 are designed to apply slice-selective magnetic field gradients (of a first polarity and a second polarity) and magnetic readout gradients. The data processing apparatus (e.g., a computer) 730 is designed to receive and process the acquired data to obtain desired images corresponding to the short T2 components. For example, the data processing apparatus can perform the dual echo subtraction.

The vessel encoded PCASL techniques described in this specification provide simultaneous perfusion images of two or more vascular territories, with SNR that is close to that of conventional ASL images with the same total scan time. The data processing techniques described in this specification enable direct estimation and correction of the relative tagging efficiencies β associated with the vessel encoding process. Advantages of these techniques over the conventional pulsed methods include higher SNR of the pseudo-continuous tagging process and spatial specificity gained from encoding of vessels within a single tagging plane.

Discrimination between two vessels depends only on separation of the vessels as they pass through the tagging plane, rather than on the identification of three dimensional slabs that contain sufficiently long segments of one vessel or the other for pulsed tagging. In addition, the temporal width of the tag bolus is naturally identical for all tagged vessels, simplifying quantitation of perfusion. As in conventional continuous or pseudo-continuous ASL, the tagging process does not need to perturb spins either proximal or distal to the tagging plane, allowing for arterial spins proximal to the tagging plane to remain relaxed for the next tagging cycle, and for the tag to be placed close to the imaging region when this is desirable. While only those vessels located along parallel lines within the tagging plane may be tagged with full efficiency, this generally does not pose a problem for encoding of 3 vessels. For encoding of 4 or more vessels, the vessels may not fall along two parallel lines. In these cases, less efficient encoding may be accepted, or new tagging pulses developed to enable curved tagging lines.

Because the tagging pulses perturb spins over a range of approximately 2 cm, a tagging plane with arterial segments that are relatively straight over this distance should be used. The minimum distance between the tagging plane and the most proximal imaging location is limited by the slice profile of the tagging pulses, and by magnetization transfer effects to approximately 2 cm.

Quantitation of perfusion using the techniques described in this specification can be the same as that for non-selective PCASL. The relative tagging efficiencies β of the vessel encoded scans are measured and included in the decoding process, resulting in decoded images that are on the same absolute scale as non-vessel encoded PCASL images. The additional terms in the signal equations for PCASL, such as those that account for the basic tagging efficiency α, the tag duration, and relaxation are scaling terms that can be treated separately from the encoding/decoding process.

The identification of optimal tagging/encoding parameters and geometries, as well as efficient techniques for prescribing these geometries have been described. The efficient separation of the three main inputs to the Circle of Willis has also been shown in this specification using two different encoding schemes as described with respect to FIGS. 4A-5B. The optimization of the techniques as described in this specification may be dependent on the interaction between the tagging parameters, the vascular geometry and the velocity distributions. For example, slower flow velocities above the Circle of Willis may call for PCASL parameters that are better tuned for those velocities. Tagging in areas of greater vessel may be improved using pulses with narrower slice profile, in order to reduce the amount of in-plane flow as blood traverses the tagging plane.

In the VEPCASL techniques as described with respect to FIGS. 1-6 above, two or more vessels flowing through the tagging plane are differentially tagged and encoded across image repetitions. Hadamard type encoding and a linear model are used to estimate the contribution of each vessel to the perfusion of each voxel. For some tagging planes, such as above the Circle of Willis, many arteries pass through the tagging plane, and unique Hadamard encoding of each vessel can be difficult.

In some implementations, additional data processing techniques can be implemented to better extract information from multiple vascular territories. In particular, the continuous nature of the spatial modulation of tagging across the tagging plane in VEPCASL can be used to identify multiple vascular territories with a small number of encoding steps. Branches of the M2 Segment of the MCA can be mapped using at least two approaches.

In VEPCASL, the relative tagging efficiency β varies periodically and roughly sinusoidally across the tagging plane from +1 to −1. In one data processing technique, the measured tagging efficiencies can be mapped to vessel coordinates. In particular, two A/P encoded images S and C are collected with the tagging modulation shifted by one half cycle in the second image. The collected images generate arterial magnetization $M_{zS} \propto \sin(2\pi y/Y)$ and $M_{zC} \propto \cos(2\pi y/Y)$, where Y is the spatial period of the modulation. At each voxel, the ASL signal is related to the location y of the source vessel by y=Y arctan (S/C)/2π, and the y position of the vascular source can therefore be localized modulo Y.

In another data processing technique, the tagging efficiencies can be measured from the data by clustering. Two or more vessel encoded images are acquired, and the relative tagging efficiency β is calculated for each voxel. For N vessel encoded images, β can be represented as a point in N dimensional space, and voxels with a common vascular source will cluster in that space. Conventional cluster analysis can then be used to identify clusters in β, and the centroid of each cluster can be used to estimate the position of the source vessel.

To obtain data, Volunteer subjects are scanned under IRB approval using the MRI system 700 such as the 3T GE scanner (from General Electric). Using the MRI system 700, images are acquired using single shot spiral imaging at 64×64 matrix, 20 cm FOV with 6 mm slices. Vessel encoding is performed as described with respect to FIGS. 1-6 above. The resultant images are shown in FIGS. 8-12. Total scan time is 8 min for FIGS. 8-10 and 12 min for FIGS. 11-12.

Figure 8:
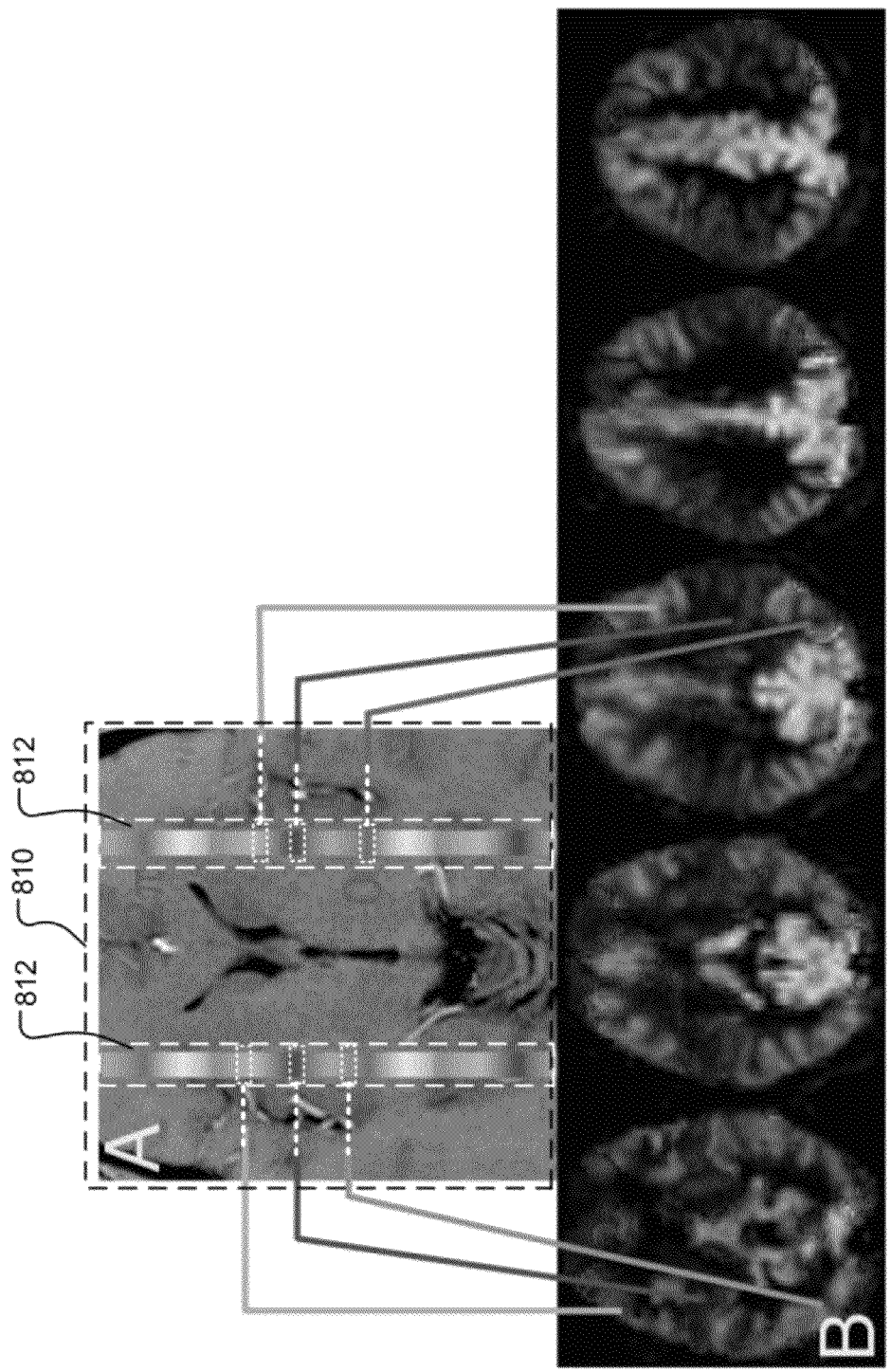
FIG. 8 shows examples of sine (sin)/cosine (cos) modulations.

FIG. 8 shows example sine (sin)/cosine (cos) modulations. For the example shown in FIG. 8, amplitude/phase (A/P) modulation of the tagging can be performed with Y=54 mm. The top image 810 represents a tagging plane. In the tagging plane, a color/shaded scale 812 is included to show the predicted phase angle arctan(S/C).

The bottom image 820 has pixel intensity proportional to the absolute ASL signal, but is colorized or shaded according to arctan(S/C), on the color or shade scale 812. For each vascular territory, the y position of the vascular source can be identified by color/shade. On both sides of the brain, three branches of the M2 segment of the MCA can be identified on both the angiogram and the vascular territory maps.

Figure 9:
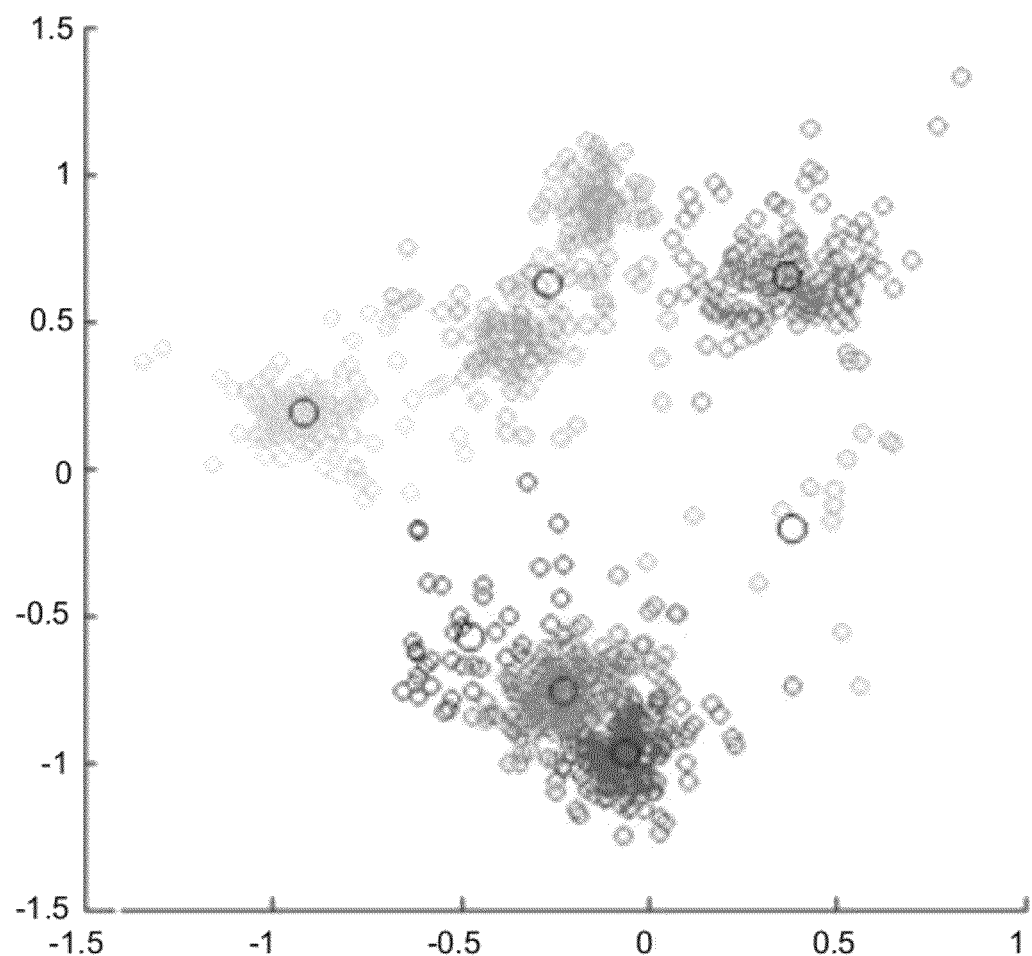
FIGS. 9, 10, 11 and 12 show example clustering techniques.
Figure 10:
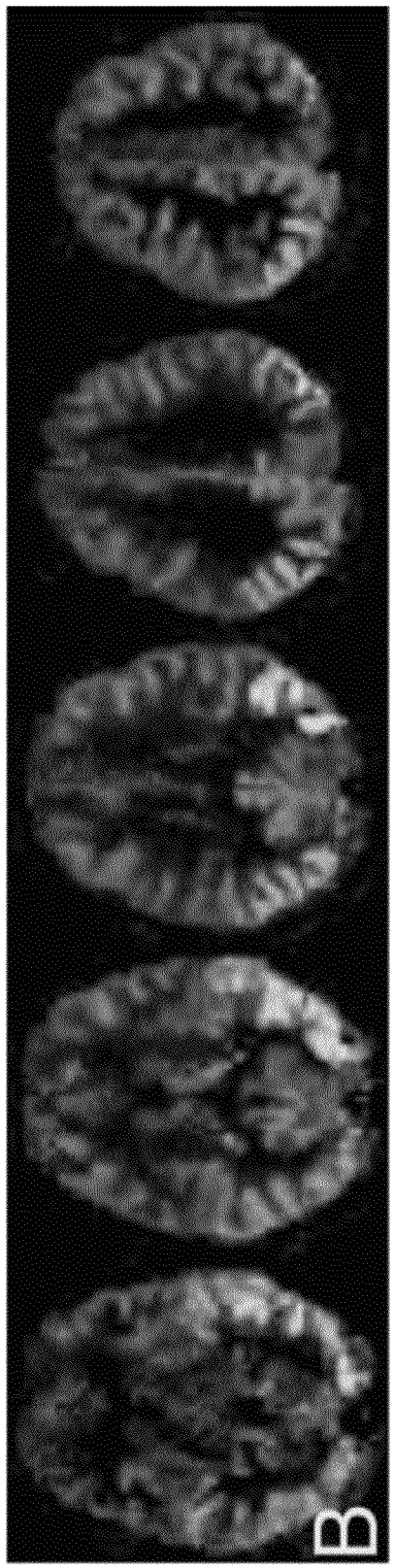

FIGS. 9-12 show example clustering techniques. Using the same data shown in FIG. 8, the clusters in two dimensional β space are shown in FIG. 9. Clusters are identified automatically using an Expectation Maximization Gaussian Mixture clustering routine in MATLAB, for example. Clusters are colorized or shaded with the same colors or shades of the corresponding voxels in FIG. 10. These techniques enable identification of the posterior branch of the MCA on the left and right sides as being different based only on slight differences in the A/P location of the arteries.

Figure 11:
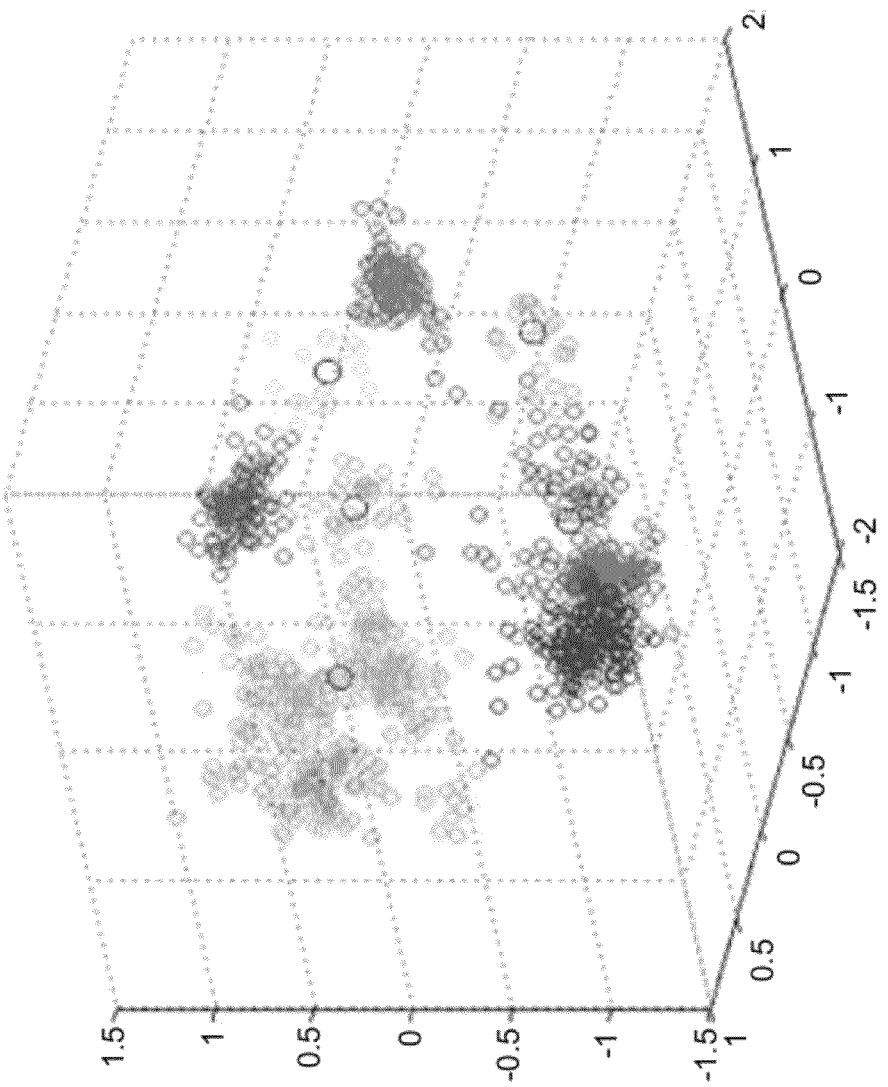
Figure 12:
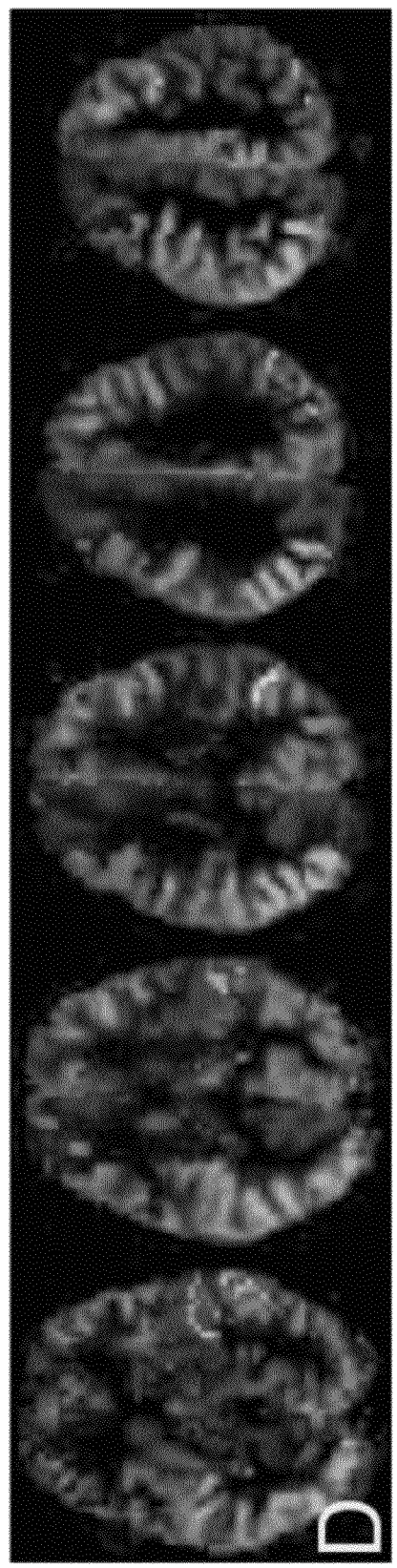

The clusters in FIG. 9 are expected to fall along a circle. However, inefficiencies in tagging due to variations in vessel curvature, flow velocities, $B_1$, and $B_0$ can cause the clusters to not fall along a circle. The phase angle in FIG. 9 is the azimuthal angle in FIG. 10. For FIGS. 11 and 12, a third data set containing L/R encoding is added to provide a clean separation between left and right source vessels. The β space and clustering are 3 dimensional, and the clusters are shown in FIG. 11. While left/right encoding is not itself of use in this case, an additional axis can separate clusters that may otherwise partially overlap, and thereby improve the accuracy of the localization of the cluster centroids.

Because VEPCASL provides a graded modulation of tagging efficiency across space, several vascular territories can be identified using a small number of encodings, limited only by the SNR of the measurement of β. At least 3 branches of each MCA can be separated at the M2 segment. The advantage of the sin/cos encoding method is that it does not depend on data fitting or clustering, and is fast and robust. The clustering based method allows for the inclusion of multiple dimensions of encoded data, which generally improves the separation of clusters. However, fully automated detection of clusters is not always robust.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a WAN, and the Internet.

The computing system may include clients and servers. A client and server are generally remote from each other and typically interact through a communication network. The relationship of client and server arises by virtue of computer programs running on the respective computers and having a client-server relationship to each other.

In addition to these variations, other modifications are possible and within the scope of the following claims.

What is claimed is what is described and illustrated, including:

1. A method for enabling mapping vascular perfusion territories comprising:
    applying a train of pseudo-continuous radio frequency tagging pulses to place two or more blood vessels of vascular perfusion territories in a tag condition and others in a control condition;
    applying a differential encoding scheme, by differentially tagging the two or more blood vessels, to fully invert or relax the blood vessels of the vascular perfusion territories;
    measuring a tagging efficiency for each blood vessel based on the applied encoding scheme, wherein the tagging efficiency for each blood vessel is proportional to a difference in magnetization in control and tag conditions; and
    separating the vascular perfusion territories by using the measured tagging efficiency in a decoding process.

2. The method as in claim 1, wherein selecting and said differentially tagging the two or more of the blood vessels comprises using pseudo-continuous arterial spin labeling.

3. The method as in claim 2, further comprising applying pulses of magnetic field gradients across a tagging plane between the train of pseudo-continuous radio frequency pulses.

4. The method as in claim 2, further comprising differentially encoding two or more of the blood vessels within the tagging plane by using a modified pseudo-continuous arterial spin labeling.

5. The method as in claim 1, further comprising applying a single labeling gradient waveform in a direction of blood flow with non-zero mean for the tag and control conditions.

6. The method as in claim 5, further comprising applying additional pulses of magnetic field gradients perpendicular to the single labeling gradient waveform to generate phase shifts between the blood vessels.

7. The method as in claim 1, wherein applying the encoding scheme comprises using a Hadamard encoding scheme.

8. The method as in claim 1, wherein measuring the tagging efficiency comprises measuring the tagging efficiency on a per-vessel basis to improve the decoding process.

9. The method as in claim 1, further comprising quantitatively measuring a perfusion of each vascular perfusion territory.

10. The method as in claim 1, further comprising measuring and quantifying a contribution of two or more of the blood vessels to the perfusion of each voxel.

11. The method as in claim 1, wherein applying the encoding scheme comprises optimizing a signal-to-noise ratio.

12. The method as in claim 1, further comprising mapping the measured tagging efficiencies to blood vessel coordinates.

13. The method as in claim 1, wherein measuring the tagging efficiencies comprises measuring the tagging efficiencies by clustering.

14. A magnetic resonance imaging (MRI) system, comprising:
an MRI imaging module to acquire MRI image; and
a controller which controls the MRI imaging module and configured to perform operations comprising:
applying a train of pseudo-continuous radio frequency tagging pulses to place two or more blood vessels of vascular perfusion territories in a tag condition and others in a control condition;
apply a differential encoding scheme, by differentially tagging the two or more blood vessels, to fully invert or relax the blood vessels of the vascular perfusion territories;
measure a tagging efficiency for each blood vessel based on the applied encoding scheme, wherein the tagging efficiency for each blood vessel is proportional to a difference in magnetization in control and tag conditions; and
separate the vascular perfusion territories by using the measured tagging efficiency in a decoding process.

15. The MRI system as in claim 14, wherein the controller is configured to select and tag the two or more of the blood vessels by using pseudo-continuous arterial spin labeling.

16. The MRI system as in claim 15, wherein the controller is configured to apply pulses of magnetic field gradients across a tagging plane between the train of pseudo-continuous radio frequency pulses.

17. The MRI system as in claim 15, wherein the controller is configured to differentially encode two or more of the blood vessels within the tagging plane by using a modified pseudo-continuous arterial spin labeling.

18. The MRI system as in claim 14, wherein the controller is configured to apply a single labeling gradient waveform in a direction of blood flow with non-zero mean for the tag and control conditions.

19. The MRI system as in claim 18, wherein the controller is configured to apply additional pulses of magnetic field gradients perpendicular to the single labeling gradient waveform to generate phase shifts between the blood vessels.

20. The MRI system as in claim 14, wherein the controller is configured to apply the encoding scheme comprising applying a Hadamard encoding scheme.

21. The MRI system as in claim 14, wherein the controller is configured to measure the tagging efficiency comprising measuring the tagging efficiency on a per-vessel basis to improve the decoding process.

22. The MRI system as in claim 14, wherein the controller is configured to quantitatively measure a perfusion of each vascular perfusion territory.

23. The MRI system as in claim 14, wherein the controller is configured to measure and quantify a contribution of two or more of the blood vessels to a perfusion of each voxel.

24. The MRI system as in claim 14, wherein the controller is configured to apply the encoding scheme comprising optimizing a signal-to-noise ratio.

25. A computer program product, embodied on a non-transitory computer-readable medium, operable to cause a data processing apparatus to perform operations comprising:
generate a train of pseudo-continuous radio frequency tagging pulses to place two or more blood vessels of vascular perfusion territories in a tag condition and others in a control condition;
perform differential encoding, by differentially tagging the two or more blood vessels, to fully invert or relax the blood vessels of the vascular perfusion territories;
measure a tagging efficiency for each blood vessel based on the applied encoding scheme, wherein the tagging efficiency for each blood vessel is proportional to a difference in magnetization in control and tag conditions; and
separate the vascular perfusion territories by using the measured tagging efficiency in a decoding process.

* * * * *